US010056069B2

(12) United States Patent
Golani et al.

(10) Patent No.: US 10,056,069 B2
(45) Date of Patent: Aug. 21, 2018

(54) WEARABLE NOISE CANCELLATION DEVICE

(71) Applicant: SILENT PARTNER LTD., Tekoa (IL)

(72) Inventors: Ori Golani, Tel Aviv (IL); Netanel Eyal, Tel Aviv (IL); Yonatan Bazak, Tekoa (IL)

(73) Assignee: SILENT PARTNER LTD., Tekoa (IL)

( * ) Notice: Subject to any disclaimer, the term of this patent is extended or adjusted under 35 U.S.C. 154(b) by 0 days.

(21) Appl. No.: 15/636,146

(22) Filed: Jun. 28, 2017

(65) Prior Publication Data
US 2017/0301337 A1 Oct. 19, 2017

Related U.S. Application Data

(63) Continuation-in-part of application No. PCT/IL2015/051259, filed on Dec. 28, 2015.

(30) Foreign Application Priority Data

Dec. 29, 2014 (IL) .......................................... 236506

(51) Int. Cl.
*G10K 11/178* (2006.01)
(52) U.S. Cl.
CPC ........ *G10K 11/1782* (2013.01); *G10K 11/178* (2013.01); *G10K 11/1788* (2013.01); *G10K 2210/3011* (2013.01); *G10K 2210/3044* (2013.01)
(58) Field of Classification Search
CPC ............. G10K 11/002; G10K 11/1782; G10K 11/1784; H04R 1/1083; H04R 3/005
See application file for complete search history.

(56) References Cited

U.S. PATENT DOCUMENTS

| 4,220,142 A | 9/1980 | Rosen et al. |
| 4,715,367 A | 12/1987 | Crossley |
| 4,788,533 A | 11/1988 | Mequignon |
| 5,416,845 A | 5/1995 | Shen |

(Continued)

FOREIGN PATENT DOCUMENTS

| CN | 2128124 | 3/1993 |
| DE | 4103912 | 8/1992 |

(Continued)

OTHER PUBLICATIONS

International Search Report for International Application No. PCT/IL2015/051259 dated Mar. 2, 2016.

*Primary Examiner* — Mohammad Islam
(74) *Attorney, Agent, or Firm* — Dorsey & Whitney LLP

(57) ABSTRACT

A noise cancelation device, and a method, for suppressing noise patterns emitted from a body of a user are disclosed. The noise cancelation device comprises in some embodiments at least one sensor for sensing noise patterns produced by the body of the user and generating noise data indicative thereof, noise cancelling circuitry configured and operable to process the noise data generated by the at least one sensor and generate anti-noise signals therefrom, and at least one acoustic transducer for producing audio outputs from the generated anti-noise signals. The noise cancelation device is configured to be attached to the body of the user, either on or adjacent a body part from which the noise patterns are being emitted.

30 Claims, 9 Drawing Sheets

(56) References Cited

U.S. PATENT DOCUMENTS

| | | | |
|---|---|---|---|
| 5,444,786 A * | 8/1995 | Raviv | A61F 5/56 381/71.11 |
| 5,477,867 A | 12/1995 | Balkanyi | |
| 5,844,996 A * | 12/1998 | Enzmann | A61B 5/7475 381/71.11 |
| 7,006,650 B1 | 2/2006 | Wild | |
| 7,317,801 B1 | 1/2008 | Amir | |
| 8,325,934 B2 | 12/2012 | Kuo | |
| 8,571,227 B2 | 10/2013 | Donaldson et al. | |
| 9,247,346 B2 | 1/2016 | Kuo et al. | |
| 2003/0235313 A1 | 12/2003 | Kurzweil et al. | |
| 2004/0234080 A1 | 11/2004 | Hernandez et al. | |
| 2007/0239225 A1 | 10/2007 | Saringer | |
| 2009/0147965 A1 * | 6/2009 | Kuo | A47C 21/003 381/71.6 |
| 2010/0124345 A1 | 5/2010 | Wiech, III | |
| 2010/0142726 A1 | 6/2010 | Donaldson | |
| 2010/0283618 A1 | 11/2010 | Wolfe et al. | |
| 2012/0163626 A1 * | 6/2012 | Booij | G10K 11/1788 381/92 |
| 2013/0204617 A1 * | 8/2013 | Kuo | H04R 3/002 704/233 |
| 2014/0169580 A1 | 6/2014 | Levitov | |
| 2014/0233748 A1 | 8/2014 | Klug et al. | |
| 2014/0268016 A1 | 9/2014 | Chow et al. | |
| 2014/0276227 A1 | 9/2014 | Perez | |
| 2017/0053637 A1 * | 2/2017 | DeFranks | A47G 9/10 |

FOREIGN PATENT DOCUMENTS

| | | |
|---|---|---|
| DE | 19626273 | 1/1998 |
| DE | 19706645 | 9/1998 |
| DE | 10115146 | 11/2001 |
| DE | 102004052845 | 5/2006 |
| DE | 102013006180 | 7/2014 |
| EP | 0168740 | 1/1986 |
| EP | 2407130 | 1/2012 |
| FR | 2651120 | 3/1991 |
| KR | 20100006935 | 1/2010 |

\* cited by examiner

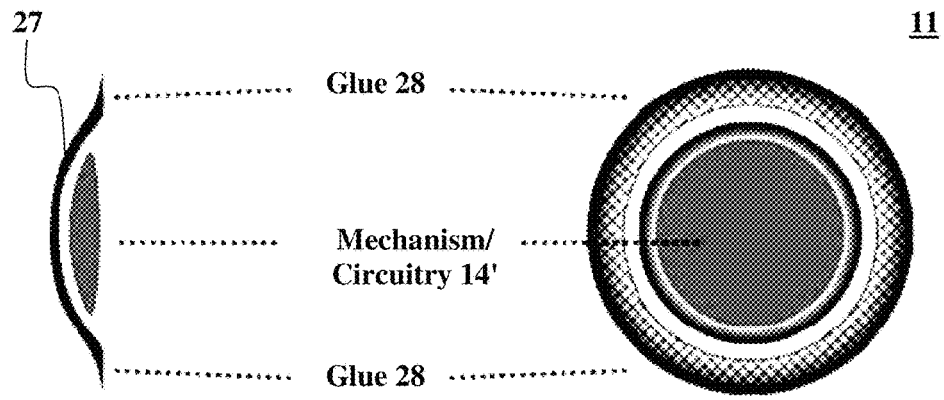
Fig. 8D
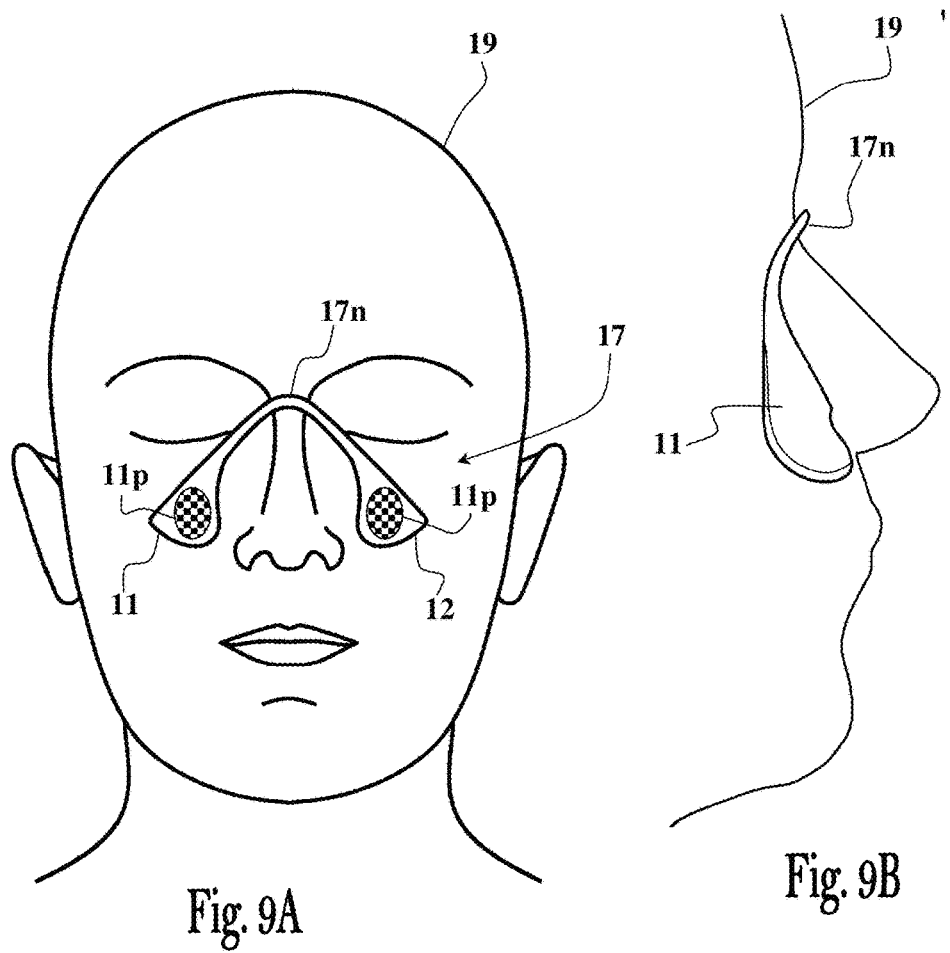
Fig. 9A
Fig. 9B

WEARABLE NOISE CANCELLATION DEVICE

TECHNOLOGICAL FIELD

The present invention is in the field of active noise cancellation. More particularly, the present invention is directed to a wearable active noise canceling device configured to attenuate bodily sounds.

BACKGROUND

Active noise cancellation (ANC) is a sound reduction method which detects undesired sounds and generates a negative copy of such sounds (anti-sound). An anti-sound is a signal of the same frequency and amplitude as the detected undesired sound, but of opposite sign. The undesired sound and outputted anti-sound destructively interfere with one another, resulting in significant noise reduction.

Most ANC systems aim to create a quiet zone around a specific spot (the listener) by suppressing unwanted sounds from a remote source or surrounding environment. Such ANC systems thus require placing the audio input and output elements in close proximity to the listener. Another approach is to place the ANC device at the noise source. This method has the advantage of reducing noise in a wide area, but only for a specific source.

For example, U.S. Pat. No. 8,571,227 describes an ANC earphone having an acoustic path including a cavity and a pipe leading to the auditory canal which are arranged to form an oscillator which in use has the effect of recovering the open loop system phase characteristics at a selected frequency or frequency range. The earphone also has two parts which can be adjusted relative to each other to allow the earphone to be comfortably and correctly positioned in use.

U.S. patent publication Nos. 2014/0169580 describes an active noise cancellation system provided in a head support to cancel noise for a supine user, lying on a bed.

U.S. Pat. No. 5,844,996 describes a system for attenuating noise which can be sensed by the auditory nerve comprising a microphone positioned in a first sound region for sensing noise present in the first sound region for creating a first electrical signal having a frequency and amplitude corresponding to the noise sensed in the first sound region. Circuitry is provided for processing the first electrical signal to create a second electrical signal having the same frequency but of opposite amplitude and sign of the first electrical signal. A speaker is provided for converting the second electrical signal to anti-noise for attenuation of the sensed noise in a second sound region spaced from the first sound region. A microphone is disposed in the second sound region for detecting any noise above a predetermined noise level in the second sound region to provide an error correction signal. Circuitry is provided responsive to the error correction signal to modify the second electrical signal to bring the noise in the second sound region so that it is below a predetermined noise level.

U.S. Pat. No. 8,325,934 describes an electronic pillow including a pillow unit encasing at least one error microphone and at least one loudspeaker in electrical connection with a controller unit, the pillow unit also including a power source, and a reference sensing unit including at least one reference microphone in electrical connection with the controller unit, the controller unit including an algorithm for controlling interactions between the error microphone, loudspeaker, and reference microphone. Unwanted noise is abated by detecting an unwanted noise with a reference microphone, analyzing the unwanted noise, producing an anti-noise corresponding to the unwanted noise in a pillow, and abating the unwanted noise.

U.S. Pat. No. 7,317,801 describes an active acoustic noise reduction system which comprises a single input transducer and an output actuator that are physically located next to each other in the same location. In one embodiment, the input transducer and the output actuator are a hybrid represented by a single element. The active noise reduction system is located as close as possible to the noise source and functions to generate an anti-noise cancellation sound wave with minimum delay and opposite phase with respect to the noise source. The noise reduction system also comprises a non-linearity correction circuit, a delayed cancellation circuit and variable gain amplifier. The system provides user control of the quiet zones generated by the system by varying the gain of the variable gain amplifier.

In spite of these developments there is a great need for further improvement in the ANC field, particularly for improving a user's comfort and improving noise reduction levels.

GENERAL DESCRIPTION

There is a need in the art for noise canceling solutions usable to devise wearable devices that can be conveniently attached to the user's body and effectively suppress noises emitted from the body of the user. Hitherto, noise cancelation applications mostly aimed at attenuating noises propagating towards a user, from a remote location or from the surrounding environment, by noise cancelation devices designed to generate quiet areas about a predefined quiet area/location i.e., the quiet location/area where noise cancelation is obtained is a remote site, far from the noise source. Though these noise cancelation techniques can attenuate noises to some degree in their predefined quiet areas, they do not provide an effective solution for cancelation of undesired noises emitted from a body of a user in the near vicinity of the "noisy" user.

The present disclosure relates to a miniaturized wearable active noise canceling device designed primarily to be worn by a user (e.g., reversibly attached over the user's face) and effectively reduce undesired noises emitted from the body of the user in areas of near proximity to the user's body (a few centimeters e.g., greater than 8 centimeters from the user's body), such as snoring produced during sleep. The inventors of the present invention found that body noises can be effectively suppressed by means of a noise cancelation device designed to be attached in the vicinity, or on, a body part of a user from which the body noises are emitted. The voice cancelation device of the present invention is thus designed for placement near (or over) a body part, preferably such that one or more acoustic sensors of the device are disposed in a vicinity of the source of the body noise, and one or more acoustic transducers of the device are disposed over the body part which carries the device so as to direct the noise canceling sounds they produce in a direction substantially perpendicular to, and away from, the surface of the body part.

The noise cancelation device of the presentation invention is thus designed to be wearable (e.g., in the form of a self-adhesive patch), non-intrusive and convenient, as well as to provide maximal noise reduction. The inventors hereof have devised a novel technique for determining the position of the acoustic transducers and sensors (microphones) of the noise cancellation device. This technique, also referred to herein as "sub-wavelength active noise cancellation", relates the distance between the source of noise to be attenuated (e.g., the user's mouth, nose, and/or throat) and the acoustic transducers, the frequency range of the undesired noises to be attenuated, and a desired attenuation factor of the noise cancelation device. More particularly, the technique comprises using a predefined relation, referred to herein as "sub-wavelength factor", which is independent of the particulars of the active noise cancellation system (such as the frequency of noise to be attenuated). For a desired attenuation factor, a suitable sub-wavelength factor may be chosen using the graph plots supplied herein, or calculated by means of computer simulation. These graph plots may be used for many possible embodiments, and do not change for different types of noise sources. Given minimal wavelength of the noise to be attenuated, the chosen sub-wavelength factor determines the maximal distance between the noise source and the acoustic transducer(s) i.e., the maximal distance is found by multiplying the chosen sub-wavelength factor by minimal wavelength of noise.

The term global noise reduction as used herein refers to the attenuation of unwanted sound, originating from one or more sources, in all space surrounding said source. This is in contrast to currently available techniques, which typically reduce noise only in limited predefined remote regions. The inventors of the present invention found that the noise cancelation device of the present invention provides effective global noise reduction of body noises, particularly when implemented according to the sub-wavelength active noise cancellation technique described hereinabove and hereinbelow.

Using this technique, the inventors have devised several possible embodiments for an active noise cancelling device specifically designed to reduce body noises in the range of 100 Hz to 1000 Hz, and possibly up to 3000 Hz, which may depend on the distance from the user, corresponding to human snoring and/or other bodily noises. This constitutes placing the acoustic transducers 1 to 7 cm from the source of the body noises (i.e., from nose and/or mouth of the user), so as to achieve an attenuation factor of about 17 to 20 dB.

Furthermore, the inventors have devised several methods of conveniently attaching the active noise cancelling device to a body part of the user.

In one aspect the present invention is directed to a noise cancelation device for suppressing noise patterns emitted from a body of a user (such as, but not limited to, body noises comprising snores, teeth grinding, mumbling, heavy breathing, stomach noises, intestine noises, flatulence, and any combinations thereof). In some embodiments the noise cancelation device comprises at least one sensor for sensing noise patterns produced by the body of the user and generating noise data indicative thereof, noise cancelling circuitry configured and operable to process the noise data generated by said at least one sensor and generate anti-noise signals therefrom (e.g., for suppressing body noises in the frequency range of 100 Hz to 1000 Hz, or in a range of 100 Hz to 3000 Hz), and at least one acoustic transducer (speaker) for producing audio outputs from the generated anti-noise signals, said noise cancelation device configured to be attached to the body of the user, either on or adjacent a body part from which said noise patterns are being emitted.

The device may be configured for placement of the at least one sensor in a vicinity and direction of the body part from which the noise patterns are being emitted. The device may be arranged such that the anti-noise sounds are produced by the at least one acoustic transducer in a direction substantially vertical to the surface of the body part to which the device is attached.

In some possible embodiments the device comprises two or more spaced-apart acoustic transducers. For example, and without being limiting, the two or more acoustic transducers may be arranged about a circumference surrounding a location on the user's body from which the noise patterns are emitted.

In some possible embodiments the device is designed to be worn by a pet/animal (e.g., canine). In this case the noise cancelling circuitry may be configured and operable to suppress noises in the frequency range of 100 Hz to 1500 Hz.

Optionally, the two or more acoustic transducers may have different frequency responses. In this case, the device may be arranged such that acoustic transducers having high-frequency response are located closer to the body part from which the noise patterns are emitted.

The noise cancelling circuitry of the device may be adapted to compensate for a frequency response of the acoustic transducers. Additionally, or alternatively, the noise cancelling circuitry may be adapted to compensate for the location of the at least one sensor relative to the body part from which the noise patterns are emitted. In some applications the noise cancelling circuitry may comprise one or more Biquad circuitries adapted to provide a desired complex frequency response.

In some possible embodiments the device may comprise a processing unit configured and operable to provide a desired frequency response of the device.

In some applications the sensor is a direct-contact sensor configured to be attached to the user's skin for sensing sound vibration therefrom.

In one application the device is arranged such that a distance of the at least one acoustic transducer from the body part from which the noise patterns are emitted is smaller than 7 cm (e.g., corresponding to a sub-wavelength factor of 0.2 in a frequency range of 100 Hz to 1000 Hz of the noise patterns). This arrangement of the device can effectively provide a minimal attenuation of the noise patterns of about 10 dB. In another possible application the device may be arranged such that a distance of the at least one acoustic transducer from the body part from which the noise patterns are emitted is smaller than 3.5 cm (e.g., corresponding to a sub-wavelength factor of 0.1 in a frequency range of 100 Hz to 1000 Hz of the noise patterns). This arrangement of the device can effectively provide a minimal attenuation of the noise patterns of about 17 to 20 dB.

In some embodiments the device comprises a resonance chamber acoustically coupled to the at least one acoustic transducer and configured to receive audio signals produced therefrom and output corresponding signals having increased intensity. Optionally, and in some embodiments preferably, the device is configured to provide a phase shift between the noise patterns produced by the body of the user and the anti-noise signals of up to 8°, and the magnitude of the anti-noise signals deviates from the magnitude of the noise patterns produced by the body of the user by about one to seven decibels.

In some applications, the device is configured to be attached to the body of the user by means of a self-adhesive patch, a nose clamp, by suspension from the user's ears or nose, or by any combination of these means.

In another inventive aspect of the present application there is provided a noise cancelation system comprising two or more of the noise cancelation devices described hereinabove, or hereinbelow, each comprising a single sensor and a single acoustic transducer, where the two or more of the noise cancelation devices are configured to be attached to the body of the user in a spaced-apart relationship in a vicinity of the body part from which the noise patterns are being emitted.

In a variant, there is provided a noise cancelation system comprising a sensor for sensing noise patterns produced by the body of the user and generating noise data indicative thereof and two or more of the noise cancelation devices, each comprising noise cancelling circuitry configured and operable to process the noise data generated by said sensor and generate anti-noise signals therefrom, and at least one acoustic transducer for producing audio outputs from the generated anti-noise signals, where the two or more noise cancelation devices are configured to be attached to the body of the user in spaced-apart relationship in a vicinity of the body part from which the noise patterns are emitted. Optionally, and in some embodiments preferably, the sensor is attached to one of the noise cancelation devices. For example, and without being limiting, at least one of the two or more noise cancelation devices and the sensor are attachable to the body of the user by means of a self-adhesive patch, a nose clamp, a suspension from the user's ears, or by any combination of these means. Optionally, and in some embodiments preferably, the noise cancelation system is shaped to form an eye mask configured to substantially cover either the right and left eyes of a user i.e., cover either one eye, both eyes, or none.

A yet another inventive aspect of the present invention is directed to a method for suppressing noise patterns emitted from a body of a subject. The method comprises sensing the noise patterns and generating noise data indicative thereof, processing the noise data and generating anti-noise signals therefrom, and producing audio outputs from the generated anti-noise signals in a direction substantially perpendicular to a surface of the body of the subject. One or more acoustic transducers may be used for producing the audio outputs within a predetermined distance from a location on the user's body wherefrom the noise patterns are emitted. This predetermined distance is preferably determined based on a minimal wavelength of the noise patterns.

Optionally, and in some embodiments preferably, a ratio between the predetermined distance and the minimal wavelength of the noise patterns is equal to or smaller than 0.5. Alternatively, the ratio between the predetermined distance and the minimal wavelength of the noise patterns is equal to or smaller than 0.2.

The method comprises in some embodiments placing at least one sensor in a vicinity of a body part of the subject from which said noise patterns are emitted for the sensing of the noise patterns.

BRIEF DESCRIPTION OF THE DRAWINGS

In order to understand the invention and to see how it may be carried out in practice, embodiments will now be described, by way of non-limiting example only, with reference to the accompanying drawings. Features shown in the drawings are meant to be illustrative of only some embodiments of the invention, unless otherwise implicitly indicated. In the drawings like reference numerals are used to indicate corresponding parts, and in which:

FIG. 3B shows an analog circuitry implementation of the filter unit, and FIG. 3C shows a digital circuitry implementation of the filter unit;

FIGS. 5A and 5B exemplify noise attenuation obtained with noise cancelation devices according to some embodiments, wherein FIG. 5A shows a graph plot of the spectrum of a recorded snoring sound, with and without the noise cancelation device according to possible embodiments, and FIG. 5B shows results of a noise cancelation experiment obtained using a possible embodiment;

FIGS. 8A to 8D show possible embodiments of the noise cancelation device and methods of attachment to the user's body, wherein FIG. 8A shows a possible embodiment employing two noise cancelation units configured for attachment at the sides of the user's nose and above the user's mouth, FIG. 8B shows a possible embodiment employing a single noise cancelation unit configured for attachment below the user's nose and above the user's mouth, FIG. 8C shows a possible embodiment employing one or more noise cancelation units in the form of adhesive patches configured for attachment over a body part of the user, and FIG. 8D shows a possible embodiment of the adhesive patch configuration shown in FIG. 8C;

FIGS. 9A to 9C schematically illustrate a possible embodiment of the noise cancelation device shown in FIG. 8A, wherein FIGS. 9A and 9B, respectively, are front and side views of the device attached to the user's face, and FIG. 9C is a sectional view of the device showing arrangement of its internal components;

DETAILED DESCRIPTION OF EMBODIMENTS

The present invention provides wearable noise cancelation devices configured for attachment to a body part of a user in close vicinity to a bodily noise source, and for effectively attenuating the noises emitted therefrom. As described and illustrated herein, the noise cancelation device of the present invention is designed to generate anti-noise signals configured to radially propagate away from the body part on which the device is mounted and destructively interfere with noises emitted from the user's body in the near vicinity thereto. In this way, the bodily noises emitted from the user are substantially attenuated at a distance of at least 8 centimeters from the body of the user, such that the bodily noises are effectively diminished/cancelled in the proximal environment of the user.

Figure 1:
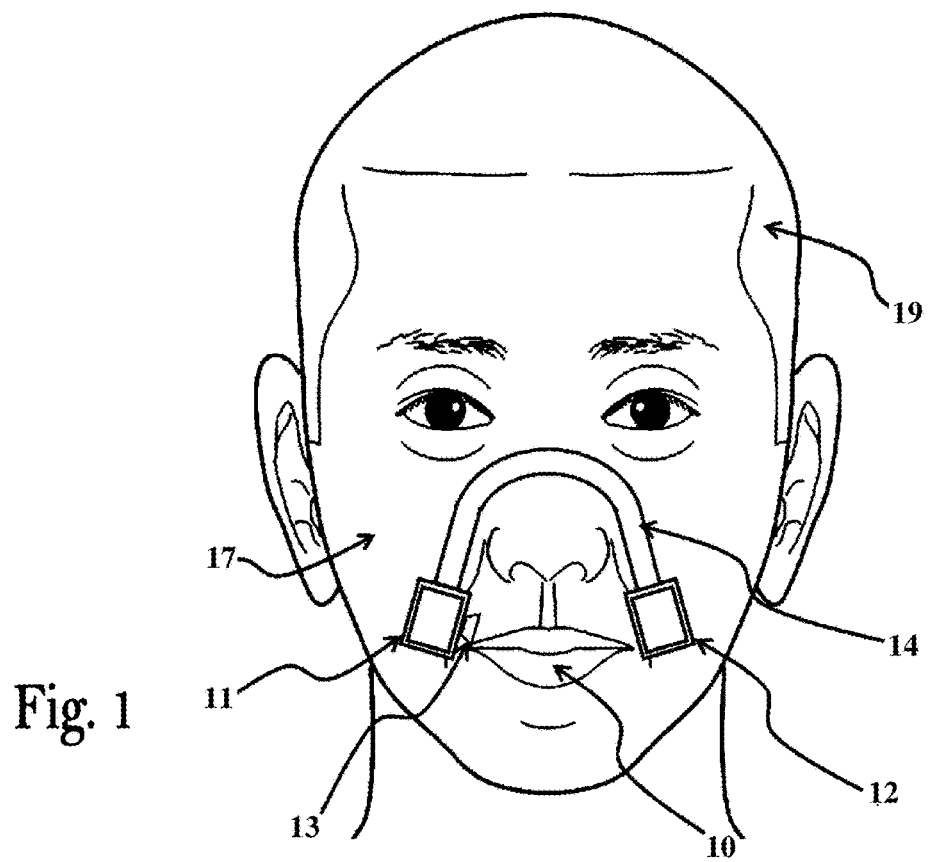
FIG. 1 illustrates a possible embodiment of the noise cancelation device, and the manner in which it may be worn by a user.

A possible embodiment of the wearable noise cancelation device 17 of the present application is exemplified in FIG. 1. In this non-limiting example noise is emitted from the user's body 19, originating mostly from the mouth 10. This noise is detected by a microphone (also referred to herein as acoustic sensor) 13 located in the vicinity of the user's mouth 10 (e.g., about 1 to 7 cm from the mouth), and analyzed by an electronic control circuit (14' in FIGS. 3A and 4) situated in a support element 14 connecting between the units of the device. The control circuit 14' is connected to two loudspeakers (also referred to herein as acoustic transducers), 11 and 12, positioned on lateral sides of the user's face (e.g., at the sides of a user's mouth 10, or nose, or on a user's cheeks), which are used to produce an anti-noise generated from the noise received from the microphone 13. The control circuit 14' generates an anti-noise, and adjusts the anti-noise, taking into account such properties of the particular embodiment used, such as the distance of loudspeakers and microphone from the noise source, number of loudspeakers used, frequency response of said loudspeakers and suchlike.

As seen in FIG. 1, the orientation of the microphone 13 is set in a direction of the user's mouth 10 to maximize its reception of the noises produced therefrom. The speakers 11 and 12 are arranged over the user's face so as to direct the outputted anti-sound away from the user's mouth/face in a (radial) direction substantially perpendicular to, and away from, the surface of the body part on which they are disposed.

In this non-limiting example the support element 14 serves both for housing the control circuit 14' and as a means of attaching the device 17 to the user's face, similar to an eyeglasses' bridge passing over the user's nose, and is further configured for electrically connecting between the control circuit 14' and the speakers 11 and 12, and the microphone 13. It is however noted that the support element 14 may be configured for placement at other locations than that exemplified in FIG. 1. For example, and without being limiting, the support element 14 may be located above, or below, the user's mouth 10. Other methods of attaching the noise cancelation device 17 are also possible, such as attaching the device 17 to the skin of the user by means of an adhesive patch. While in this non-liming example the microphone 13 is shown attached to loudspeaker 11, it may be similarly attached to the other loudspeaker 12, or to the bridging element of the control circuit 14. Optionally, two (or more) microphones 13 are used in the noise cancelation device, located in the vicinity of the user's mouth in a spaced-apart relationship e.g., each being attached to one of the loudspeakers and oriented in direction of the user's mouth 10.

Ideal noise cancelation (i.e., for achieving complete elimination of all noise) requires the loudspeakers to be placed in the same location of the noise source. In practice this is not feasible, as discomfort to the user will be too severe. Placing the loudspeakers too far from the noise source will create loud and quiet areas, where the interference of noise and anti-noise is constructive and destructive, respectively. In order to achieve global noise reduction such loud areas cannot be tolerated.

The inventors of the present invention have developed a novel ANC concept, referred to hereinafter as sub-wavelength ANC. According to the sub-wavelength ANC concept of the present invention, in order to effectively attenuate undesired body noises, the loudspeakers used to output the anti-noise sounds are disposed at a distance from the source of the noise (e.g., the user's mouth 10) that is smaller than the wavelength of the undesired noises to be attenuated by the device (e.g., the distance between the user's mouth 10 and each of the loudspeakers 11 and 12 being smaller than a minimal wavelength of the noise). For example, and without being limiting, in order to substantially suppress most body sounds of the user, typically having frequencies in the range of 100 Hz to 1 KHz, the distance between each one of the loudspeakers and the user's mouth 10 may be set to about 1 to 7 cm. The sub-wavelength ANC approach of the present invention avoids the loud and quiet areas associated with conventional ANC, thereby providing global noise reduction. Placing the loudspeakers symmetrically about the noise source also serves to improve noise reduction.

Figure 2:
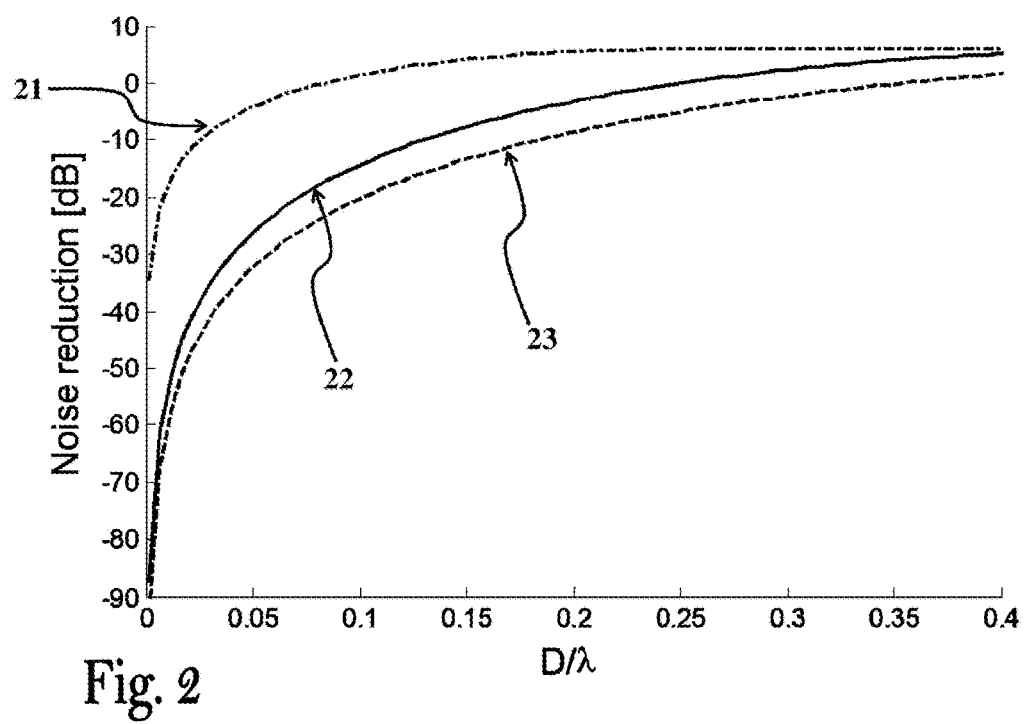
FIG. 2 shows graph plots of maximal attainable noise reduction as a function of loudspeaker distance, for several loudspeaker configurations, according to some possible embodiments.
Figure 6:
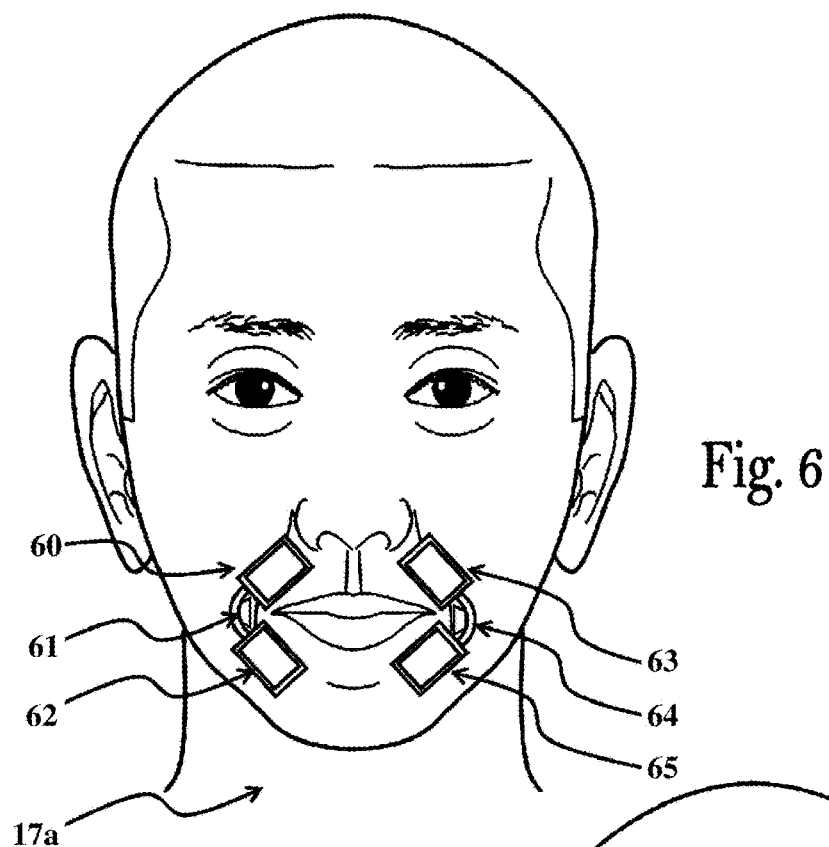
FIG. 6 illustrates a possible embodiment of the noise cancelation device utilizing four loudspeakers.

FIG. 2 shows graph plots presenting the maximal achievable noise reduction level as a function of the ratio of the distance between the noise source and the loudspeakers (D) and the wavelength of the noise ($\lambda$). Results for three configurations are shown, as follows: plot 21 presenting a single-speaker configuration (e.g., the embodiment shown in FIG. 1 with loudspeaker 12 disconnected), plot 22 presenting a two-speaker configuration (as shown in FIG. 1), and plot 23 presenting a four-speaker configuration (exemplified in FIG. 6).

The sub-wavelength factor, $D/\lambda$, determines the maximal achievable noise reduction. For example, and without being limiting, with reference to the two speaker plot 22 in FIG. 2, to obtain noise reduction of at least 17 dB, a sub-wavelength factor of $D/\lambda \leq 0.1$ is required e.g., D<3.5 cm for noise frequencies of up to 1000 Hz. If a reduction of 10 dB is sufficient, then the sub-wavelength factor may be $D/\lambda \leq 0.2$ (e.g., D<7 cm for noise frequencies of 1000 Hz). In some embodiments, this is the main parameter according to which the distance between the loudspeakers and the noise source is determined (i.e. the shortest wavelength in the frequency range of interest determines the distance).

In one non-limiting example, the loudspeakers used may not be identical (i.e. will have different frequency responses). In such cases, the result shown in FIG. 2 indicates that it is advantageous to place those speakers with good high-frequency response closer to the mouth than speakers having good low-frequency response. Using this concept, an improvement in overall frequency response may be achieved while maintaining a convenient design.

The microphone 13 may be a type of a small microphone device, such as an electret microphone. These types of microphones are typically a few millimeters in size, making them suitable for a small wearable device as described herein. A non-limiting example of such a device is the ABM series microphones, as manufactured by Pro-Signal Co. The loudspeakers 12, 13 may be a type of miniaturized speakers, similar to those used in cellular and smartphone applications. A non-limiting example of such a device is the BoomSound speakers, as manufactured by HTC Co. Using miniaturized loudspeakers serves two purposes; as the largest element of an ANC system is usually its loudspeakers, the use of a miniature version enables the device to be compact and suitable for wearable applications. As the speakers are very small they also have low directivity, i.e. they broadcast sound in a wide angular range. This serves to improve the range in which efficient noise reduction is achieved.

In a possible embodiment as exemplified in FIG. 1, the loudspeakers 11 and 12 can be placed 3 cm from the user's mouth 10, corresponding to a worst-case noise reduction of about 17.5 dB in the relevant frequency range (100 Hz-1000 Hz for human snoring), and much better than that for average cases. The four-speaker configuration 17A exemplified in FIG. 6 offers an even better noise reduction, by symmetrically placing four loudspeakers (60, 62, 63, and 65) around the noise source (i.e., the user's mouth 10). This provides approximately 5 dB additional noise reduction compared to the two-speaker configuration, albeit at a cost of more hardware.

Figure 3A:
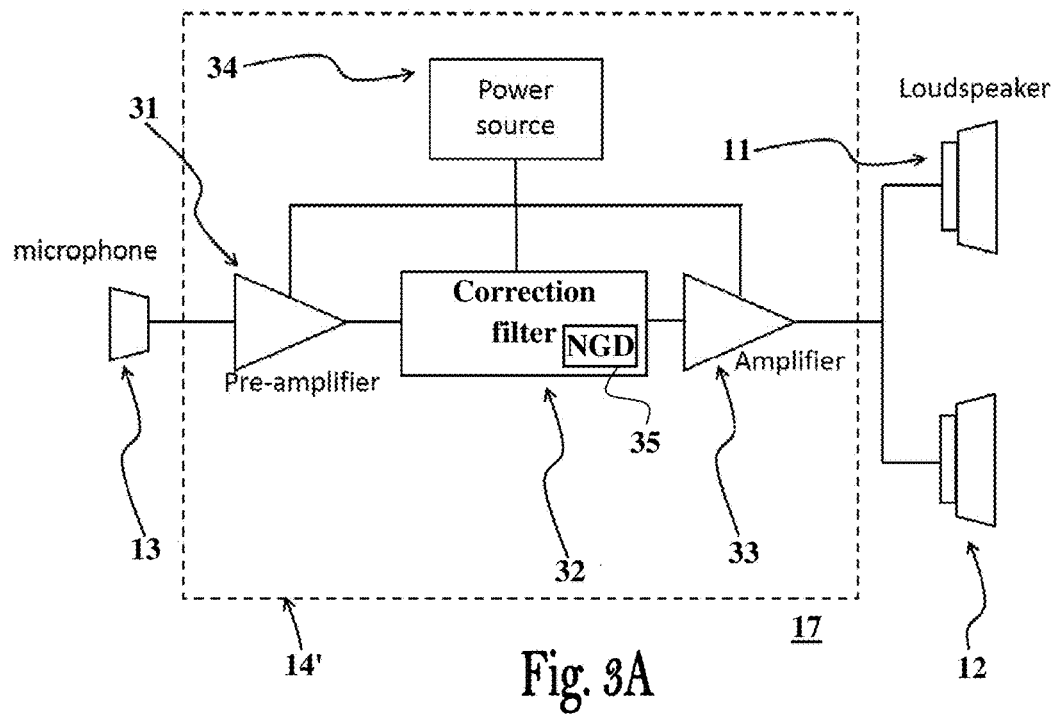
FIGS. 3A to 3C are block diagrams of a control circuitry of the noise cancelation device according to possible embodiments, wherein FIG. 3A schematically illustrates the control circuitry.
Figure 3B:
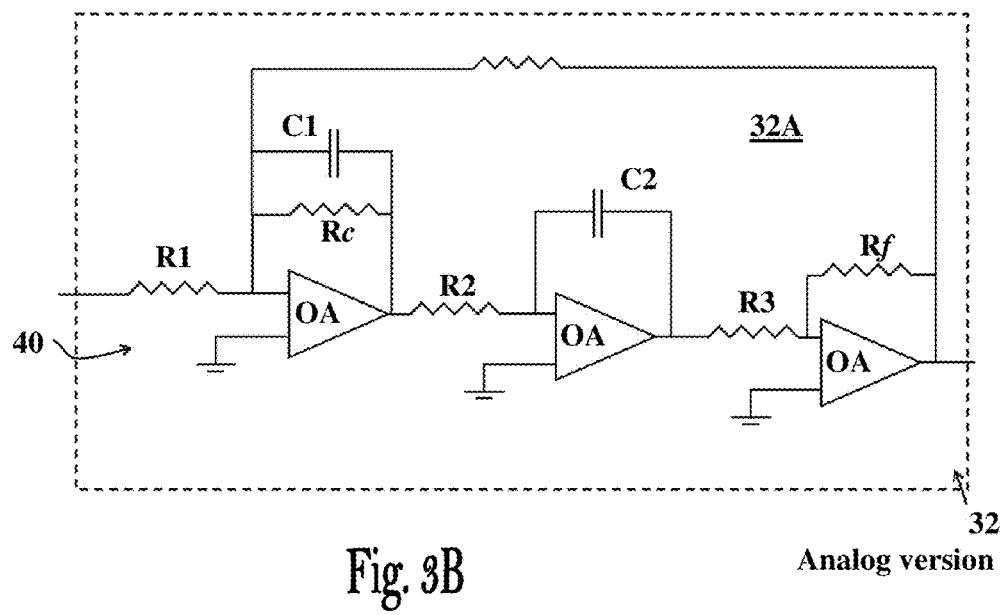

FIGS. 3A to 3B show block diagrams of the control circuitry 14' according to some possible embodiments. Signal detected by the microphone 13 is amplified by pre-amplifier 31 and passed through an equalization filter 32. The sub-wavelength ANC approach of the present invention (i.e., setting the distance between the loudspeakers 11 and 12 and the noise source to be smaller the wavelength of the noise) substantially simplifies the filter design, without requiring multiple correction microphones. The ultimate goal of the filter is to provide a flat phase and amplitude response of the anti-noise signal, throughout the frequency range of interest, and set the appropriate amplitude and phase of the anti-noise. In addition, it is important that no new noise is generated in frequencies outside the range of interest. To achieve this, the filter is required to do the following: compensate for the frequency response of the loudspeakers, 12 and 13, account for the number of loudspeakers, and compensate for the location of the microphone(s). The first task is achieved by means of designing a filter whose frequency response is the inverse of the frequency response of the loudspeaker. Cascading of the frequency response of the loudspeaker with that of the filter will thus provide a flat frequency response.

The number of loudspeakers determines the filter gain. Generally, ideal performance is achieved when the amplitude of noise is equal to that of the total anti-noise (i.e. the combined anti-noise produced by all loudspeakers). Therefore, in some embodiments, if the number of loudspeakers is N, the gain of the filter will be 1/N. Slight variations of this number can be used to optimize the overall response, e.g. by compensating for the slight signal reduction caused by placing the microphone(s) at a greater distance from the noise source. In addition, the filter must compensate for the phase accumulated by the sound wave as it travels from the noise source to the microphone. This is achieved, in some embodiments, by a negative group-delay (NGD) circuitry 35, providing a negative group delay proportional to the distance of the microphone from the user's mouth. The negative group delay circuitry 35 essentially unravels the effect of mouth to microphone distance, making the exact location of the microphone(s) less important (although it is still advantageous to keep it close to the mouth, as it simplifies the required group delay circuitry and improves signal quality).

Figure 3C:
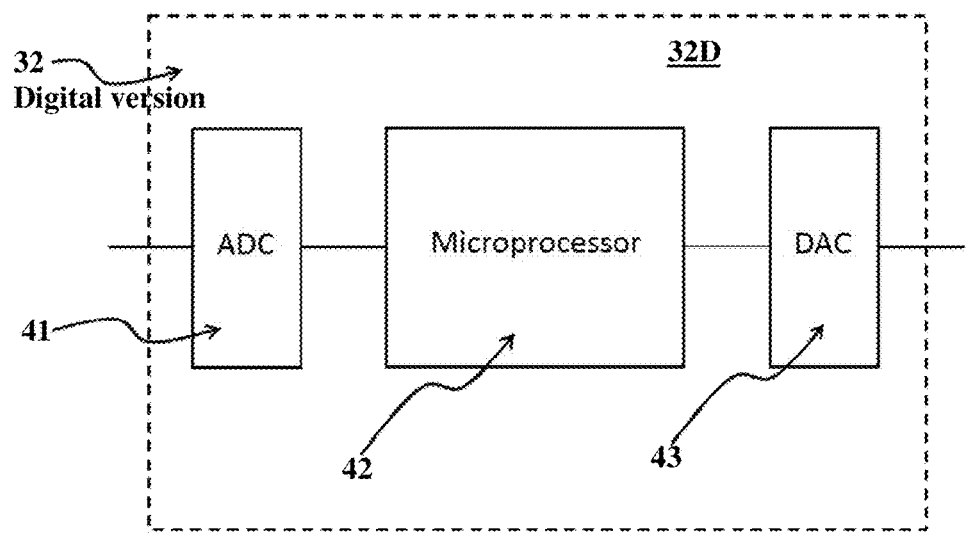

These three goals may be achieved using a single correction filter unit 32, one which takes into account all of the relevant effects. The requirements of the correction filter 32 are independent of its specific implementation, and therefore it might be implemented as either an analog or a digital device. FIGS. 3B and 3C show two possible embodiments of the filter 32, an analog implementation 32A and a digital implementation 32D, respectively. The analog version 32A exemplified in FIG. 3B is based on connecting multiple operational amplifiers (OAs), resistors (R1, R2, ... ), and capacitors (C1, C2, ... ), in order to achieve the desired transfer function. In one non-limiting example, these components are connected in a form of a Tow-Thomas biquad configuration 40, which enables a versatile design of the circuit's frequency response. Several such circuits can be cascaded to achieve an arbitrarily complex frequency response. The digital implementation 32D exemplified in FIG. 3C consists of an analog-to-digital converter (ADC) 41, which is used to convert the amplified (from amplifier 31) signal from the microphone (13) to the digital domain, a microprocessor 42, which applies the needed frequency response to the digital signal obtained from the microphone, and a digital-to-analog converter (DAC) 43, which translates the digital signal back to the analog domain for output via the loudspeakers.

Referring back to FIG. 3A, following the filter 32, a power amplifier 33 is used to drive the speakers 11 and 12, and its gain may be adjusted to compensate for power variations in the signal. A key requirement for this embodiment is miniaturization of the circuit. All active circuit elements 31, 32, 33, and the power source 34 are placed within the control circuit 14 to achieve a compact and convenient design. Low power consumption is also of high priority, as small batteries are essential for compact realization.

Figure 4:
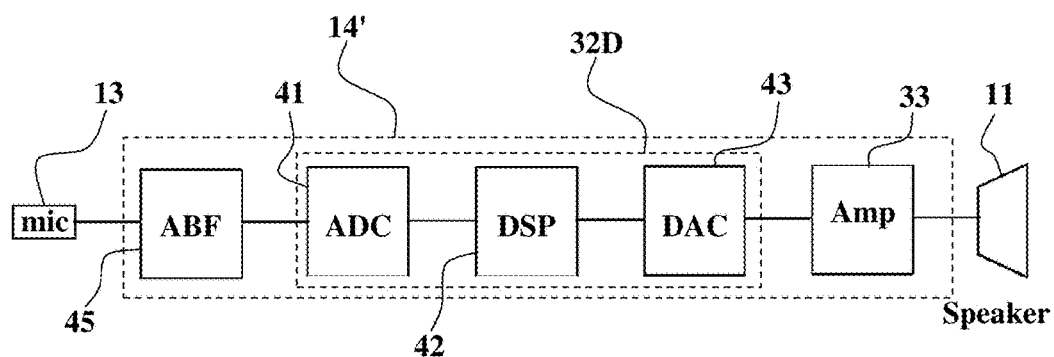
FIG. 4 is a block diagram of another possible implementation of the control circuitry employing the digital circuitry implementation of the filter unit.

FIG. 4 shows another possible embodiment of the control circuitry 14' employing a digital filter implementation 32D as shown in FIG. 3C. In this embodiment the signals received by the microphone 13 are passed through an analog (or digital) band-pass filter (ABF/digital filter e.g., a Bessel filter of the first order) 45 configured to filter out low frequency components of the received signals to remove noise, and also filter high frequency components in order to prevent aliasing effects. In this case, the digital filter unit 32D is further configured to compensate the phase shift introduced by the analog band-pass filter 45 and caused due to the time delay of the filter unit 32D.

In some embodiments the digital filter 32D is implemented as an infinite impulse response (IIR) filter configured to compensate for the transfer function of the system (e.g., including transfer function components associated with distance of noise source to the microphone, delay and and/or distortions introduced by the microphone, the amplifiers, the circuitry board, and or the speakers) and/or the resonance chamber etc., and designed to shift the phase of the received noise signal by 180 degrees. Thus, in order to provide full/maximal cancelation, the transfer function of the filter ($H_{target}(f)$) should satisfy the following requirement:

$$H_{target}(f) = -\frac{1}{H_{speaker-mic}(f)} \cdot e^{2\pi i f \tau}$$

where $H_{speaker-mic}(f)$ is a transfer function of the speaker and microphone being used in the device, and $\tau$ is a delay time of the digital elements of the device. In this way, the ratio between the input and output signals is substantially |1| in amplitude, thereby providing high audio volume at the output of the device and a 180° phase shift i.e., phase inversion. Digital IIR filters are therefore preferable candidates in some embodiments, as they require substantially less mathematical operations and digital memory resources, as compared to finite impulse response (FIR) filter implementations. It is thus appreciated that IIR filters are more suitable for real-time systems and exhibit minimal time delays of their digital components. It is however noted that in some embodiments the device is implemented using FIR filter for improved stability.

Figure 5A:
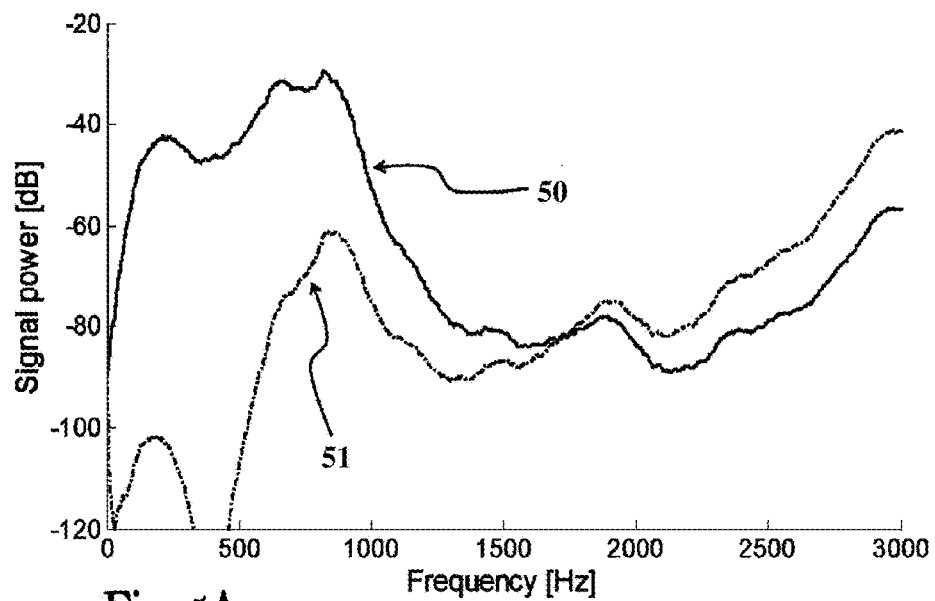
Figure 5B:
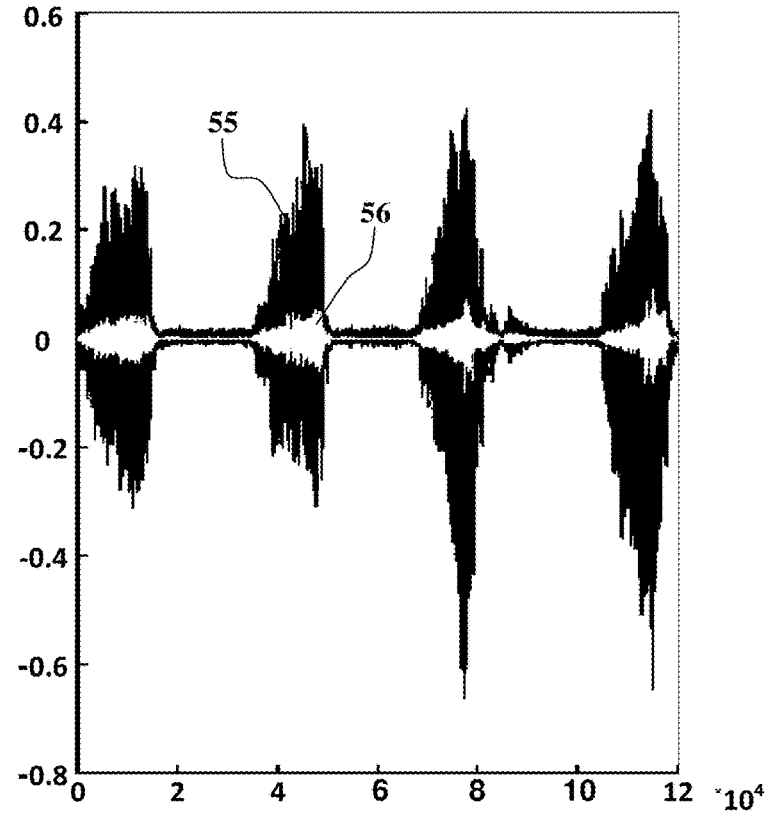

FIGS. 5A and 5B show test results obtained using the control circuitries exemplified in FIGS. 3 and 4. FIG. 5A shows graph plots of simulation results obtained with a spectrum of a recorded snoring sound, where plot 50 is the original spectrum without the use of the noise canceling system, and plot 51 is the sound spectrum after the noise canceling device 17 was used to suppress the snoring noise 50. FIG. 5B shows spectrum of a recorded snoring sound 55 and of an attenuated sound 56 obtained in a test conducted using an embodiment of the noise cancelation device shown in FIG. 9C. The experiments conducted by the inventors showed that optimal noise cancelation results can be achieved when a phase shift smaller than 8° is obtained between the bodily noises acquired by the microphone and the anti-noise signals generated by the device (i.e., the phase shift between bodily noises and the anti-noise produced by the device is in a range of 172° to 188°), and the audio volume of the generated anti-noise signals (i.e., magnitude of output signal) deviates from the bodily noises by about one to seven decibels, so the cancellation will be effective.

In the embodiments the audio volume of the generated anti-noise signals deviates from the bodily noises by about one to seven decibels, and the phase shift between the bodily noises acquired by the microphone and the anti-noise signals generated by the device is up to 10° (i.e., the phase shift between bodily noises and the anti-noise produced by the device is in a range of 170° to 190°, or up to 12° (i.e., the phase shift between bodily noises and the anti-noise produced by the device is in a range of 168° to 192°. In addition, in some embodiments the phase shift between the bodily noises and the anti-noise signals is up to 8°, 10° or 12°, and the audio volume of the generated anti-noise signals deviates from the bodily noises by about one to seven decibels.

Another possible embodiment (exemplified in FIG. 8C) of the noise cancelation device is based on two or more separate subsystems, each comprising a single loudspeaker, single microphone 13 and a control circuit 14'. This enables higher freedom in placing the loudspeakers independently of each other, giving greater flexibility of design at the cost of more components. This embodiment also enables adding more loudspeakers as required, obtaining better noise level reduction (such as described in the four-speaker configuration shown in FIG. 6). When using this embodiment, each separate noise cancelation device may be attached to the user's face by means of a self-adhesive patch.

Figure 7:
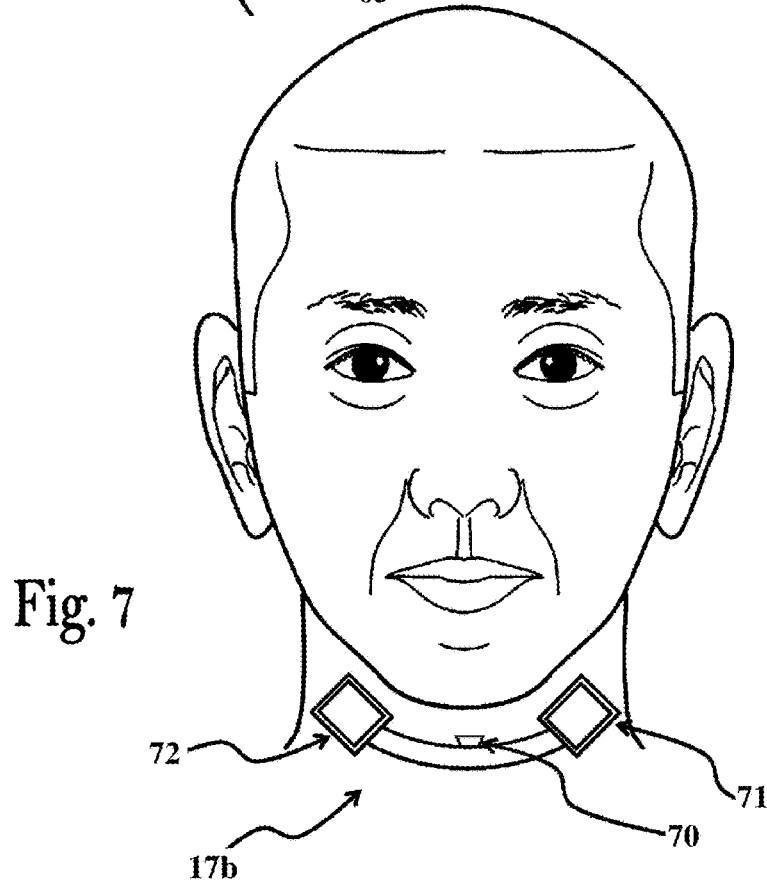
FIG. 7 illustrates a yet another possible embodiment of the noise cancelation device configured for positioning on the user's throat.

According to yet another possible embodiment the noise cancelation device is configured for placement of the loudspeakers on the user's throat. This possible embodiment advantageously eliminates low frequency sounds emitted from the throat (rather than the mouth and nose as exemplified in previously discussed embodiments), such as growling sounds produced by the user. Such an embodiment 17B is exemplified in FIG. 7, and consists of two or more loudspeakers (71, 72) worn by the user in a necklace-like configuration. The microphone 70 can be either a standard microphone, such as microphone 13 shown in FIG. 1, or a direct-contact microphone, attached to the user's skin for sensing sound vibration through the skin tissue, rather than through the air. The direct contact alternative has the benefit of improving the signal acquisition of the system, as the signal detected by the direct contact microphone will be only that emitted by the user, and not by the user's surroundings. In this non-limiting example the microphone 70 is located more or less on a central line along the throat (e.g., beneath the user's chin), and the loudspeakers 71 and 72 are placed towards the sides of the user's throat.

It goes without saying that noise cancelation device 17 of the present invention may be similarly attached to any body part/organ from which undesired noises might be emitted. Accordingly, embodiments of the invention may be used to substantially attenuate/cancel body noises produced by the stomach, intestine and/or anus, of the user. For this purpose embodiments of the noise cancelation device may be configured for placement over an upper portion, mid portion, and/or lower portion, of the user's belly, and/or over the user's buttocks.

Figure 8A:
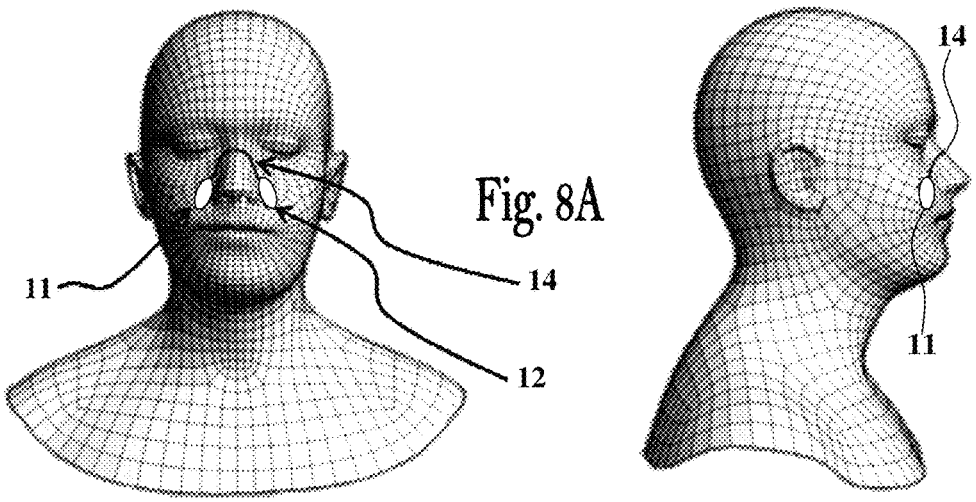
Figure 8B:
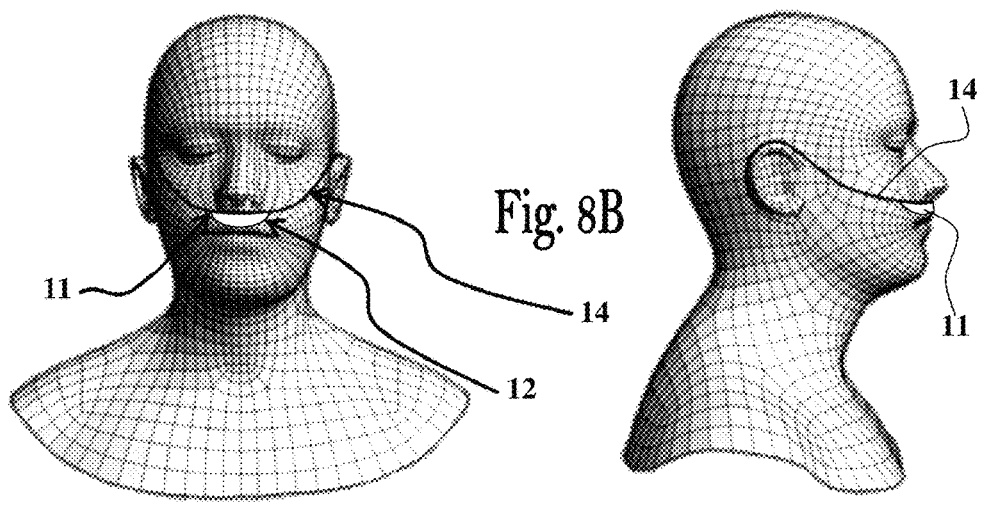
Figure 8C:
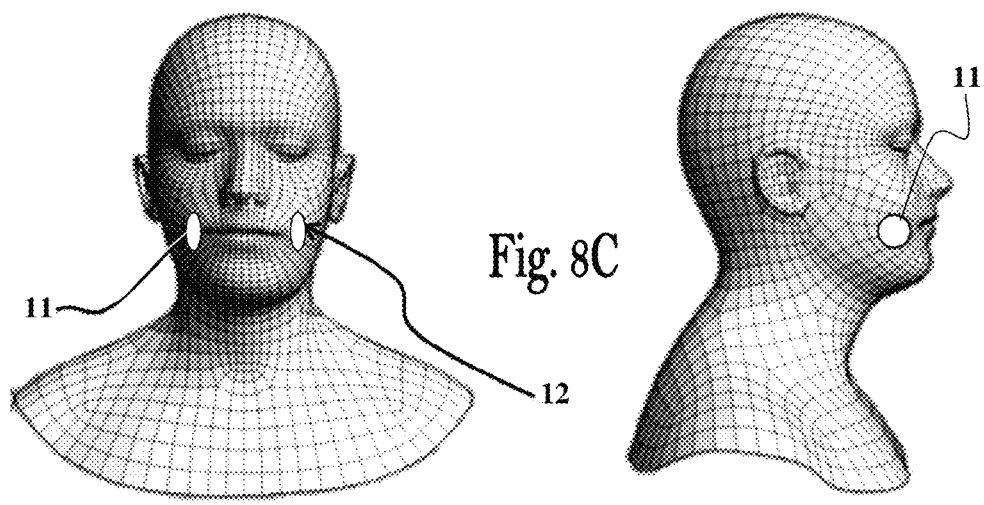

As described hereinabove, there are many possible methods of attaching the ANC device to the user. A compact and convenient design is necessary to ensure user comfort. FIGS. 8A to 8C demonstrate possible attachment methods and device designs. In FIG. 8A, an eyeglasses-like clamp design is shown, where the method of attachment utilizes a clamp/support element (14) positioned about the user's nose. FIG. 8B shows a suspension attachment method, where the device is suspended from the user's ears. FIG. 8C shows an attachment method by means of one or more adhesive patches. Needless to say, each of these possible designs may be adapted to each of the aforementioned embodiments (shown in FIGS. 1 and 5 to 7), including the use of multiple loudspeakers.

FIG. 8D shows a possible embodiment of the adhesive patch configuration shown in FIG. 8C. In this non-limiting example, the control circuit 14' is placed under a membrane 27 provided with one or more layers of adhesive material 28 at a circumferential periphery of the membrane for attachment to a body part of the user. The membrane 27 may be manufactured from a thin, and/or perforated, film/membrane suitable for passage of the anti-noise signals produced by the control circuit 14' therethrough.

Figure 9C:
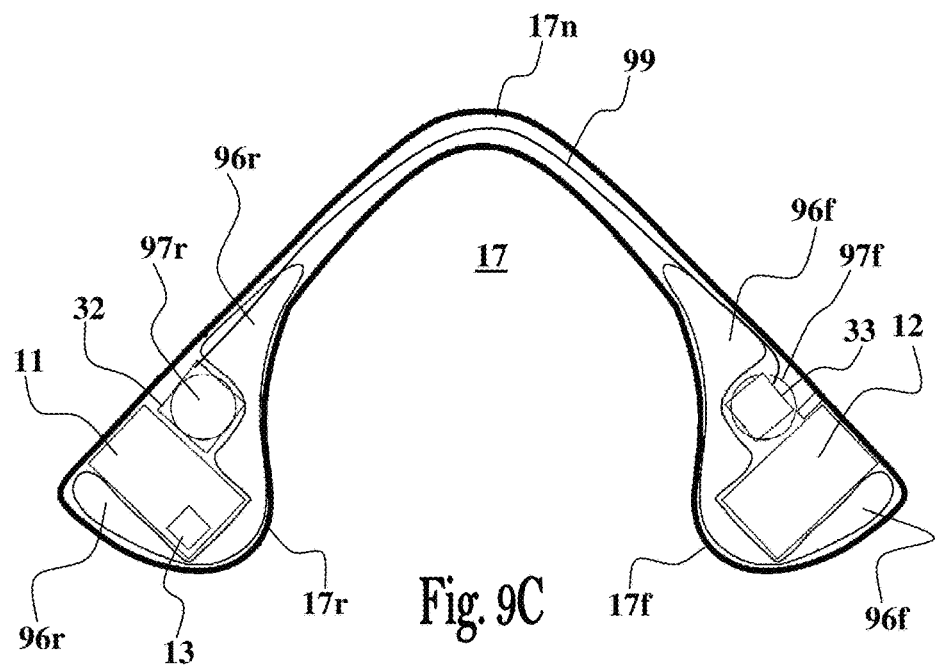

FIGS. 9A to 9C schematically illustrate a possible embodiment of the noise cancelation device 17 implemented as a "Λ"-shaped unit having right and left lobes (with respect to the user's face), 17r and 17f respectively, connected by a nose bridge 17n. As seen in FIGS. 9A and 9B, the right and left lobes, 17r and 17f, are configured to be positioned at the sides of the nose of the user 19, under the right and left eyes, respectively.

As seen in FIG. 9C, showing a sectional view of the noise cancelation device 17, each of the right and left lobes, 17r and 17f, is configured to accommodate a loudspeaker, 11 and 12 respectively, at least one battery, 97r and 97f respectively, and a resonance chamber 96r and 96f. The right lobe 17r further comprises a control unit 32 and a microphone 13, and the left lobe further comprises a power amplifier 33. Electric wires 99 passing through the nose bridge are used to electrically connect between the electric components disposed in the right and left lobes, 17r and 17f. the electric wires 99 may be used to transfer anti-noise signals generated by the control unit 32 in the right lobe 17r to the power amplifier 33 located in the right lobe, and for transferring the amplified anti-noise signals generated by the power amplifier 33 to the loudspeakers 11 and 12 located in the right and left lobes respectively.

Each of the resonance chambers, 96r and 96f, is acoustically coupled to a respective loudspeaker, 11 and 12 respectively, and being comprised of the volume segments of the respective lobe not being occupied by electrical components of the device 17. Optionally, and in some embodiments preferably, the volume of each of the resonance chambers, 96r and 96f, is set to about 0.5 to 0.9 cc, and in some other embodiments 0.7 to 1.3 cc, so as to amplify the signal produced by the loudspeakers by resonance. More particularly, interior surfaces of the resonance chamber are configured to reflect acoustic waves, such that when an acoustic wave enters the resonance chamber, it bounces back and forth within the chamber with low losses in a standing wave effect. As additional wave energy enters the resonance chamber, it combines with and reinforces the standing wave, thereby increasing its intensity.

The resonance chambers 96r and 96f each define an enclosed space that has an opening acoustically coupled to the respective speaker, 11 and 12, where the sound wave enters and exits after bouncing off the internal walls producing the resonance effect. Thus, the materials the resonance chambers 96r and 96f are made of, particularly of the actual internal walls (or of one or more coating layers applied thereover), its shape and the position of the opening, as well as the finish (porosity) of the internal walls (or coating), are factors configured to optimize the final resulting sound produced. In this way improved sensitivity of the speakers is obtained, and the power consumed by the device is substantially reduced. With this design of the device, the size of the device can be reduced, since smaller batteries can be used to power the device.

The lobes and/or the nose-bridge of the noise cancelation device 17 may be manufactured from any suitable elastic, flexible, or non-elastic/flexible, and/or medical grade material, using any suitable manufacture process e.g., 3D printing, mold pressing, etc.

Figure 10:
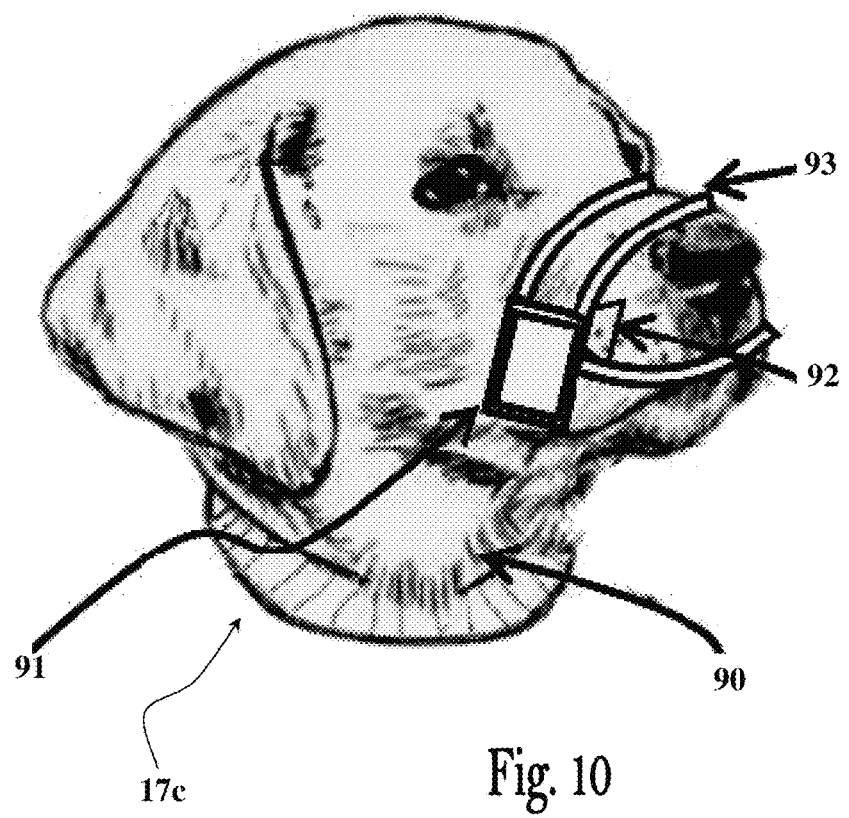
FIG. 10 schematically illustrates a possible embodiment of the noise cancelation device configured to be attached to an animal.

A noise cancellation device based on the principles described hereinabove can also be adapted to non-human users, particularly pets/dogs. FIG. 10 exemplifies a possible embodiment of the noise cancelation device 17c, designed to suppress the sound of a dog's barks. In this non-limiting example the loudspeakers 91 and microphone 92 are placed on the dog's muzzle 93. The noise cancelation device operates in the same manner as described hereinabove, and benefits from the same principles of the ANC sub-wavelength approach of positioning and multiple loudspeakers. The noise cancelation device 17c is adapted to the higher noise power emitted by the dog, as well as the frequency range of its barks (typically about 100 to 1500 Hz). Customization of these parameters according to dog breed and size is also possible.

Figure 11:
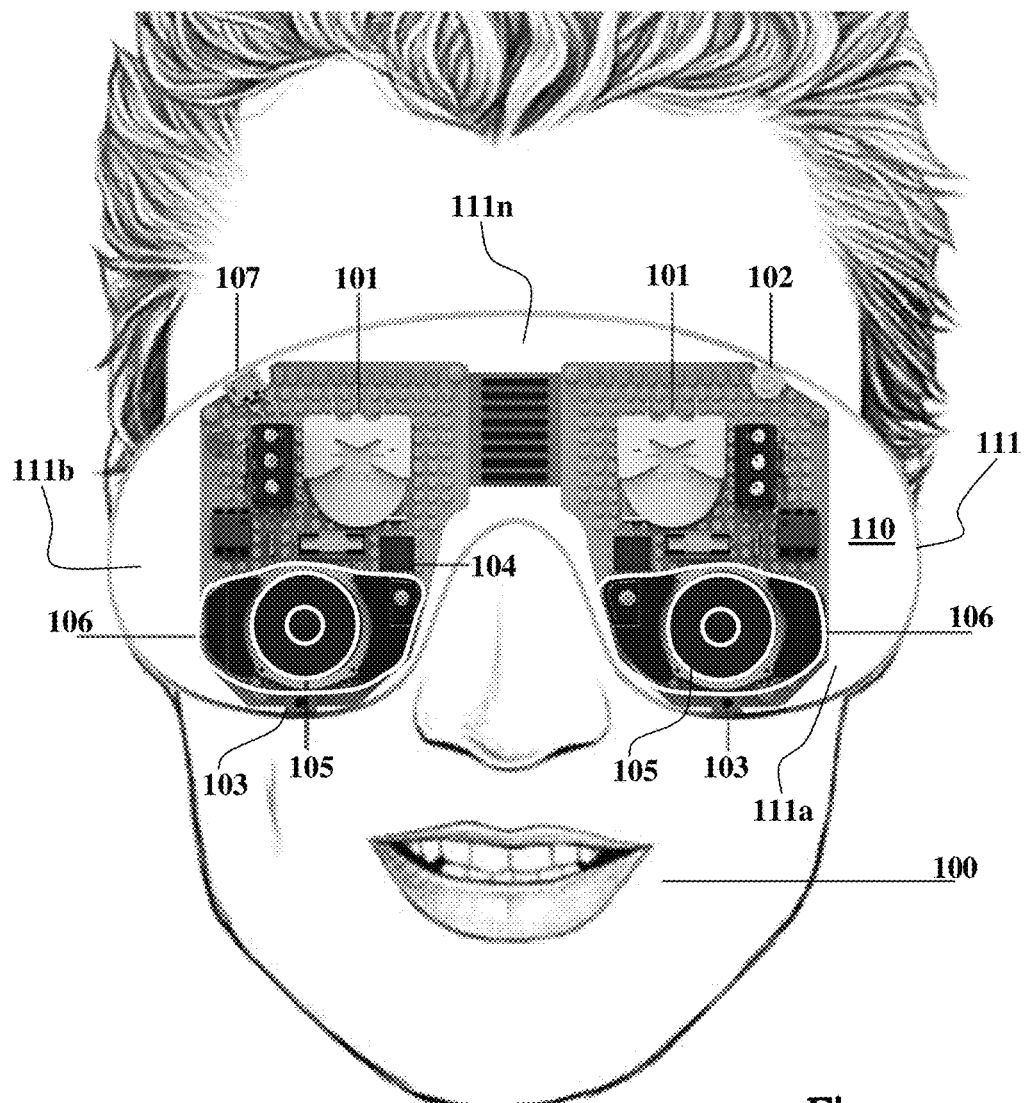
FIG. 11 schematically illustrates a configuration of the noise cancellation device according to some possible embodiments in a form of an eye mask.

FIG. 11 shows a non-limiting illustration of an eye mask configuration 110 of a wearable noise cancellation device, according to some possible embodiments. Optionally, and in some embodiments preferably, the eye mask noise cancellation device 110 is a type of active sub-wavelength noise cancellation device, as described hereinabove. The noise cancellation 110 comprises a flexible/bendable support 111 comprising of two tear-shaped lobes, 111a and 111b, connected one to the other by their narrow tapering regions to form a nose support portion 111n of the flexible/bendable support 111. As seen, the tear-shaped lobes 111a and 111b are configured to cover the right and left eyes of the user, and substantially block/prevent passage of light to the user's eyes.

Accordingly, the eye mask noise cancellation 110 is designed to be placed over the eyes of the user so as to place the noise canceling device 110 at a sub-wavelength distance from the source of the emitted sound/noise i.e., the user's mouth 100, which is to be cancelled. The noise cancellation device 110 can be powered by one or more rechargeable (or disposable non-chargeable) batteries 101, and can be activated and deactivated by means of a master switch device 102. In this specific and non-limiting example, the noise cancellation device 110 comprises two batteries 101 (e.g., button cell batteries), wherein each battery 101 is connected by a suitable battery socket mounted on a respective one of the tear-shaped lobes 111a and 111b.

The noise cancellation device 110 comprises one or more acoustic sensors (microphones) 103 located at the vicinity of the noise source 100, and configured to convert the sound/noise pressure into electric signals. In this specific and non-limiting example, the noise cancellation device 110 comprises two acoustic sensors 103, each of which located at a bottom region of a respective one of the tear-shaped lobes 111a and 111b i.e., a region near an edge of the wider portion of each lobe located as close as possible to noise source.

The noise cancellation device 110 also comprises one or more speakers 105; in this specific example two speakers 105 are used, wherein each speaker 105 is located on a respective one of the lobes 111a and 111b i.e., on both sides of the noise source 100, such that they are positioned at a sub-wavelength distance therefrom. Optionally, and in some embodiments preferably, each speaker is mounted inside a respective resonance chamber 106. The electric signals generated by the acoustic sensors 103 are analyzed by an electronic circuitry 104, such as a microcontroller, configured and operable to generates corresponding anti-sound/noise signals for generating by the speakers 105 sound/noise cancelation audible outputs.

In some embodiments, the noise cancellation device 110 is equipped with an electrical connector e.g., micro USB port 107, for charging the batteries 101, which can be also used for updating the firmware of the microcontroller 104. Optionally, and in some embodiments preferably, the electronic circuitry 104 is configured to generate right-side anti-sound/noise signals corresponding to the electric signals generated by the right acoustic sensor 103 mounted on the right tear-shaped lobe 111a, and which are to be output by the right speaker 105 of the lobe 111a, and left-side anti-sound/noise signals corresponding to the electric signals generated by the left acoustic sensor 103 mounted on the left tear-shaped lobe 111b, and which are to be output by the left speaker 105 of the lobe 111b. In some embodiments each tear-shaped lobe, 111a and 111b, comprises a respective electronic circuitry 104 configured to analyze/process the electric signals generated by the acoustic sensor 103 mounted therewith on same tear-shaped lobe, and which are to be output by the respective speaker 105 mounted therewith on same tear-shaped lobe.

Optionally, the flexible/bendable support 111 of the noise cancellation device 110 comprises a see-through opening (not shown) in substantially at a center of at least one of the tear-shaped lobe 111a and 111b, to thereby allow the user to see the surrounding environment while wearing/using the noise cancellation device 110.

It is noted that the terms such as top and bottom, right and left, and similar adjectives used herein in relation to orientation of the elements and components of the noise cancellation device disclosed herein, refer to the manner in which the illustrations are positioned on the paper, not as any limitation to the orientations in which the elements/components of the noise cancellation device can be used in actual applications.

As described hereinabove, and exemplified in the figures, the noise cancelation device of the present invention can be implemented in a form of a self-adhesive patch configured be attached to user's skin in the vicinity (or over) a body part from which the undesired noises are emitted (e.g., user's mouth or throat). Particularly, the noise cancelation device of the present invention is designed for placing at least one microphone in the vicinity and direction of the body part emitting the undesired noises, and placing at least one loudspeaker for outputting the anti-noise within a predetermined distance from the noise source smaller than the minimal wavelength of the undesired noises to be suppressed by the device. The at least one loudspeaker is attached to the user's body so as to direct the produced anti-noise in a radial direction relative to a central axis (or point) of the user's body or of an organ of the user, or substantially vertical to the surface of the body part to which the noise cancelation is being attached i.e., to direct the anti-noise away from the surface of the user's body part or organ (e.g., head, neck, etc.).

While particular embodiments of the invention have been described, it will be understood, however, that the invention is not limited thereto, since modifications may be made by those skilled in the art, particularly in light of the foregoing teachings. As will be appreciated by the skilled person, the invention can be carried out in a great variety of ways, employing more than one technique from those described above, all without exceeding the scope of the invention.

The invention claimed is:

1. A noise cancelation device for suppressing noise patterns emitted from a body of a user, the noise cancelation device comprising:
   at least one sensor for sensing noise patterns produced by the body of the user and generating noise data indicative thereof;
   noise cancelling circuitry configured and operable to process the noise data generated by said at least one sensor and generate anti-noise signals therefrom; and
   at least one acoustic transducer for producing audio outputs from the generated anti-noise signals;
   wherein said noise cancelation device is configured to be attached to the body of the user, either on or adjacent a body part from which said noise patterns are being emitted.

2. The noise cancelation device of claim 1, configured for placement of the at least one sensor in a vicinity and direction of said body part from which the noise patterns are being emitted.

3. The noise cancelation device of claim 1, arranged such that the anti-noise sounds are produced by the at least one acoustic transducer in a direction substantially vertical to the surface of the body part to which the device is attached.

4. The noise cancelation device of claim 1, further comprising two or more spaced-apart acoustic transducers, wherein said two or more acoustic transducers are arranged about a circumference surrounding a location on the user's body from which the noise patterns are emitted.

5. The noise cancelation device of claim 4 wherein the two or more acoustic transducers have different frequency responses, the device is arranged such that acoustic transducers having high-frequency response are located closer to the body part from which the noise patterns are emitted.

6. The noise cancelation device of claim 1 wherein the noise patterns are body noises comprising at least one of the following: snores; teeth grinding; mumbling; heavy breathing; stomach noises, intestine noises, or flatulence.

7. The noise cancelation device of claim 1 wherein the noise cancelling circuitry is configured and operable to suppress body noises in a frequency range of 100 Hz to 1000 Hz.

8. The noise cancelation device of claim 1, designed to be worn by an animal.

9. The noise cancelation device of claim 8 wherein the noise cancelling circuitry is configured and operable to suppress noises in a frequency range of 100 Hz to 1500 Hz.

10. The noise cancelation device of claim 1 wherein the noise cancelling circuitry is adapted to compensate for a frequency response of the at least one acoustic transducer.

11. The noise cancelation device of claim 1 wherein the noise cancelling circuitry is adapted to compensate for the location of the at least one sensor relative to the body part from which the noise patterns are emitted.

12. The noise cancelation device of claim 1 wherein the noise cancelling circuitry comprises one or more Biquad circuitries adapted to provide a desired complex frequency response.

13. The noise cancelation device of claim 1, further comprising a processing unit configured and operable to provide a desired frequency response of the noise cancelling circuitry.

14. The noise cancelation device of claim 1 wherein the at least one sensor includes a direct-contact sensor configured to be attached to the user's skin for sensing sound vibration therefrom.

15. The noise cancelation device of claim 1, further comprising a resonance chamber acoustically coupled to the at least one acoustic transducer and configured to receive audio signals produced therefrom and output corresponding signals having increased intensity.

16. The noise cancelation device of claim 1, configured to provide a phase shift between the noise patterns produced by the body of the user and the anti-noise signals is up to 8°, and the magnitude of said anti-noise signals deviates from said noise patterns produced by the body of the user by about one to seven decibels.

17. The noise cancelation device of claim 1, configured to be attached to the body of the user by means of a self-adhesive patch.

18. The noise cancelation device of claim 1, configured to be attached to the body of the user by means of a nose clamp.

19. The noise cancelation device of claim 1, configured to be attachable to the body of the user by means of suspension from the user's ears.

20. A noise cancelation system, comprising:
   a sensor for sensing noise patterns produced by the body of the user and generating noise data indicative thereof; and
   two or more of the noise cancelation devices of claim 1 each of which includes noise cancelling circuitry configured and operable to process the noise data generated by said sensor and generate anti-noise signals therefrom and at least one acoustic transducer for producing audio outputs from the generated anti-noise signals, said two or more noise cancelation devices configured to be attached to the body of the user in spaced-apart relationship in a vicinity of the body part from which the noise patterns are emitted.

21. The noise cancelation system of claim 20 wherein the sensor is attached to one of the noise cancelation devices.

22. The noise cancelation system of claim 20, wherein at least one of the two or more noise cancelation devices and the sensor are attachable to the body of the user by a self-adhesive patch.

23. The noise cancelation system of claim 20, wherein at least one of the two or more noise cancelation devices and the sensor are attachable to the body of the user by a nose clamp.

24. The noise cancelation system of claim 20, wherein at least one of the two or more noise cancelation devices and the sensor are attachable to the body of the user by suspension from the user's ears.

25. The noise cancelation system of claim 20, configured as an eye mask.

26. A method for suppressing noise patterns emitted from a body of a subject using the noise cancelation device of claim 1, the method comprising:
   sensing said noise patterns by the at least one sensor and generating noise data indicative thereof;

processing said noise data by the noise cancelling circuitry and generating anti-noise signals therefrom; and using the at least one acoustic transducer for producing audio outputs from the generated anti-noise signals in a direction substantially perpendicular to a surface of the body of the subject.

27. The method of claim 26, further comprising positioning one or more acoustic transducers for producing the audio outputs within a predetermined distance from a location on the user's body wherefrom the noise patterns are emitted, said predetermined distance is determined based on a minimal wavelength of the noise patterns.

28. The method of claim 27 wherein a ratio between the predetermined distance and the minimal wavelength of the noise patterns is equal to or smaller than 0.5.

29. The method of claim 28 wherein a ratio between the predetermined distance and the minimal wavelength of the noise patterns is equal to or smaller than 0.2.

30. The method of claim 26, further comprising placing at least one sensor in a vicinity of a body part of the subject from which said noise patterns are emitted for the sensing of the noise patterns.

* * * * *